(12) United States Patent
Hardt

(10) Patent No.: US 8,021,530 B2
(45) Date of Patent: Sep. 20, 2011

(54) METHOD FOR SEPARATION OF CHEMICAL SUBSTANCES AND/OR PARTICLES, DEVICE AND ITS USE

(75) Inventor: Steffen Hardt, Darmstadt (DE)

(73) Assignee: Istitut fur Mikrotechnik Mainz GmbH, Mainz (DE)

( * ) Notice: Subject to any disclaimer, the term of this patent is extended or adjusted under 35 U.S.C. 154(b) by 1324 days.

(21) Appl. No.: 10/578,602

(22) PCT Filed: Nov. 9, 2004

(86) PCT No.: PCT/EP2004/012650
§ 371 (c)(1),
(2), (4) Date: May 8, 2006

(87) PCT Pub. No.: WO2005/050185
PCT Pub. Date: Jun. 2, 2005

(65) Prior Publication Data
US 2007/0045184 A1 Mar. 1, 2007

(30) Foreign Application Priority Data
Nov. 14, 2003 (DE) .................................. 103 53 406

(51) Int. Cl.
*G01N 27/447* (2006.01)
*G01N 27/26* (2006.01)
*B01D 17/06* (2006.01)

(52) U.S. Cl. ... 204/450; 205/775; 210/511; 210/748.01; 210/649; 210/634

(58) Field of Classification Search .................. 204/554, 204/451, 453, 601, 603; 210/85, 94, 96.1, 210/511, 654, 739, 745, 748, 198.2, 243, 805, 649, 634, 635, 656; 436/180, 518, 526, 514, 172, 6, 177, 52, 53, 150, 161, 178; 422/81, 82, 82.08, 50, 101, 186.01, 186.06, 186.1; 366/336; 435/6, 91.2, 259
See application file for complete search history.

(56) References Cited

U.S. PATENT DOCUMENTS

| 5,716,852 A * | 2/1998 | Yager et al. ................... 436/172 |
| 6,541,213 B1 * | 4/2003 | Weigl et al. .................... 435/7.1 |
| 7,261,812 B1 * | 8/2007 | Karp et al. ................. 210/198.2 |

(Continued)

FOREIGN PATENT DOCUMENTS
DE 37 42 292 6/1989
(Continued)

OTHER PUBLICATIONS

C.W. Theos et al., *Electroextraction Two-Phase Electrophoresis*, Applied Biochemistry and Biotechnology, vol. 54, (1995), pp. 143-157.

(Continued)

*Primary Examiner* — Jeffrey T Barton
*Assistant Examiner* — Jennifer Dieterle
(74) *Attorney, Agent, or Firm* — Hudak, Shunk & Farine Co. LPA

(57) ABSTRACT

Electric fields are applied parallel to and/or vertical to the interfaces on adjacent microfluid lamellae made of nonmiscible media containing said biomolecules and bioparticles to which they have different physico-chemical affinities in order to separate biomolecules and bioparticles and the biomolecules and bioparticles are electrophoretically separated.

2 Claims, 9 Drawing Sheets

U.S. PATENT DOCUMENTS

| | | | |
|---|---|---|---|
| 2002/0153046 A1* | 10/2002 | Dantsker et al. | 137/833 |
| 2003/0159999 A1* | 8/2003 | Oakey et al. | 210/695 |
| 2004/0104173 A1* | 6/2004 | Manach et al. | 210/656 |

FOREIGN PATENT DOCUMENTS

| | | |
|---|---|---|
| DE | 199 30 253 | 12/2000 |
| DE | 694 27 690 | 5/2002 |
| DE | 100 63 096 | 9/2002 |
| DE | 101 13 257 | 11/2002 |
| EP | 1 353 172 | 10/2003 |
| WO | 00/22428 | 4/2000 |
| WO | WO 02082072 * | 10/2002 |
| WO | 03/066191 | 8/2003 |

OTHER PUBLICATIONS

S. Devasenathipathy, et al., *Electrokenetic Particle Separation*, $7_{th}$ International Conference on Miniaturized Chemical Biochemical Analysis Systems, Oct. 5-9, 2003, pp. 845-848.

T. Herweck, et al., *Visualization of Flow Patterns and Chemical Synthesis in Transparent Micromixers*, Microreaction Technology, Proceedings of the Fifth International Conference on Microreaction Technology, 2001, pp. 215-229.

V. Reddy, et al., *Organic/Aqueous Two Phase Microflow for Biological Sample Preparation*, $7^{th}$ International Conference on Miniaturized Chemical and Biochemical Analysis Systems, Oct. 5-9, 2003, pp. 437-440.

C.-L. Liu, et al., *Partitioning of Proteins Using Two-Phase Aqueous Surfactant Systems*, AIChE Journal, Apr. 1995, vol. 41, No. 4, pp. 991-995.

V.G. Gaikar, et al., *The Effect of Surface Active Additives on the Partitioning of Proteins and Enzymes in Aqueous Two-Phase Systems*, J. Chem. Tech. Biotechnol., 1996, vol. 67, pp. 329-332.

D. Raymond, et al., *Continuous Sample Pretreatment Using a Free-Flow Electrophoresis Device Integrated onto a Silicon Chip*, Analytical Chemistry, 1994, vol. 66, No. 18, pp. 2858-2864, XP-000478030.

F. Hachem, et al., *Hydrophobic Partitioning of Proteins in Aqueous Two-Phase Systems*, Enzyme and Microbial Technology, vol. 19, 1996, pp. 507-517, XP-002316648.

T. Herweck, et al., *Visualization of Flow Patterns and Chemical Synthesis in Transparent Micromixers*, Microreaction Technology, Proceedings of the Fifth International Conference on Microreaction Technology, 2002, pp. 215-229.

* cited by examiner

METHOD FOR SEPARATION OF CHEMICAL SUBSTANCES AND/OR PARTICLES, DEVICE AND ITS USE

FIELD OF THE INVENTION

The invention concerns a method for separation of chemical substances and/or particles, a device suitable for this, as well as its use.

BACKGROUND OF THE INVENTION

In the field of assaying of complex mixtures of biomolecules, such as protein or nucleic acids, one often uses electrophoresis methods. Especially suitable for this are capillary electrophoresis and isoelectric focusing, but also 2D gel electrophoresis. In recent years, electrophoresis systems in particular have been miniaturized in the form of biochips. This ensures that one can also work with small specimen quantities, the analysis can be highly automated, and the electrophoresis step can be coupled directly to the sample preparation step. This leads to high throughput rates.

In DE 101 13 257 C1 is described an electrophoresis device for analysis of specimens, isolation, purification and preparative recovery of chemical substances, which can be configured as a ready-made miniaturized chip. By means of this chip, one can carry out a two-dimensional electrophoresis. At first, the substances being separated are isoelectrically focused. The pre-separated substances are then separated by capillary gel electrophoresis in second separation channels, arranged perpendicular to the first separation channel.

Two-phase systems are also suitable for protein separation. A protein sample is introduced into a dispersed, generally aqueous two-phase system. Depending on their chemical affinity, the proteins distribute themselves among the different phases. The dispersed phases are then separated after a certain time, making use of the different densities of the two liquid phases. This method is described, e.g., in F. Hachem et al., "Enzyme and Microbial Technology" 19:507-517, 1996.

According to V. G. Gaikar, "J. Chem. Tech. Biotechnol." 1996, 67, pages 329-332, cationic and anionic surfactant additives are used to support the separation of the proteins. These increase the hydrophobicity of the proteins. A two-phase system based on polyethylene glycol, on the one hand, and sodium sulfate solution, on the other hand, was used. The separating of proteins by means of two-phase, aqueous, surfactant systems was also investigated more closely in C. L. Liu et al., "AIChE Journal", 1995 Vol. 41, No. 4, pages 991-995.

In V. Reddy et al., "Proceedings of the 7$^{th}$ International Conference on Miniaturized Chemical and Biochemical Analysis Systems", 5-9 Oct. 2003, Squaw Valley, Calif. USA, pages 437-440, the organic-aqueous liquid extraction based on phenol for the purifying of DNA is described. In order for the individual cell fragments investigated there to be well distributed in the two fluid phases, a two-phase microfluid stream is used, which uses electrodynamic instabilities to enlarge the active surface on which a transition from one phase to the other can occur. The membrane and protein fragments accumulate in the organic phase, while the DNA remains behind in the aqueous phase.

Micromixers are often used for the efficient blending of substances, such as are described, e.g., in T. Herweck et al. "Proceedings of the 5$^{th}$ International Conference on Microreaction Technology, 2001, pages 215-229. Its functional principle is based on the fact that alternatingly arranged, laminar flowing, very thin fluid sheets make possible a mixing of the substances being mixed simply by diffusion.

In S. Devasenathipathy et al., "Proceedings of the 7$^{th}$ International Conference on Miniaturized Chemical and Biochemical Analysis Systems, Oct. 5-9, 2003, Squaw Valley, Calif. USA, pages 845-848, charged colloidal particles in a solution are separated by means of electrokinetic processes. Two buffer streams with different ionic conductivities are introduced into a T-shaped channel system, containing the particles being separated. By applying an electric field, the particles are extracted from the stream with lower conductivity and enriched in the stream with higher conductivity.

In C. W. Theos et al., "Applied Biochemistry and Biotechnology", Vol. 54, 1995, pages 143-157, under the heading "Electroextraction", an electrophoretic separation across the phase boundaries is undertaken by applying an electric field to an aqueous two-phase system. Mixtures of two kinds of proteins were separated in a region between isoelectric points, with oppositely charged particles being accumulated in separated phases. The influence of the electrostatic potential on the protein separation in the region of the phase boundaries was investigated at greater length.

SUMMARY OF THE INVENTION

The aim of the present invention is to propose separation methods and a suitable device for this, wherein additional separation parameters are made use of as compared to classical electrophoresis methods.

This aim is achieved by methods as well as a device, and its use according to the claims.

The invention is based on the combination of electrophoresis methods and separation methods via two-phase systems so as to not only separate chemical substances and particles in terms of their mass, but also at the same time making use of other criteria, such as the physicochemical affinity of the chemical substances or particles for different phases or their phase boundaries. In this way, a multidimensional separation and analysis becomes possible.

Separation is used here synonymously with analysis, purification, and preparative recovery.

In a special variant, one makes use of the special properties of microfluid systems: in the millimeter to submillimeter range and smaller, the surface tensions act much more strongly on fluid sheets than do the volume forces or the force of gravity. In this way, one can collect the most varied liquids of differing density in a system of different fluid sheets, without them becoming deposited according to their density.

By sheets in the context of this invention is meant, in particular, long, narrow strips of fluid and/or gel with a preferably roughly rectangular cross section, while the sheets preferably have a width of 1 μm to 1000 μm and also have similar dimensions in terms of height. The length of the sheets is preferably in the mm to cm range.

The miniaturization by the use of microfluid systems means that even the smallest of specimen quantities can be automated and processed in very short time. High throughput technologies of this kind are especially required for the analysis of complex mixtures of biomolecules. One topical example at present is proteomics research, where they are trying to clarify the functional relationship between genetic information and the protein content of the cells. The methods and the device according to the invention make it possible to carry out very many assays in short time and thereby separate and analyze complex mixtures of proteins, nucleic acids and cell fragments.

When an electric field is applied in parallel with the phase boundary of at least one sheet, a very sensitive multidimensional separation is achieved by the electrophoretic separation along at least one sheet or the phase boundary surfaces in combination with the affinity of the chemical substances or particles for the phases and phase boundary surfaces. Even substances and particles with very similar properties in regard to the separation method can be separated in this way.

This separation process is facilitated by applying an additional electric field perpendicular to the phase boundary or boundaries.

An especially good efficiency of separation is achieved by the use of a microfluid system with a plurality of sheets of two or more different phases. By increasing the number of phase boundaries, the parameter of the permeability of the phase boundaries becomes more important as a separating criterion. By "phase" is meant primarily the chemical composition of a medium, such as a liquid or a gel.

Thus, several sheets of a phase can be present, alternating with sheets or one or more other phases. One can also use systems in which only one sheet is present for each phase.

The separating efficiency can also be achieved by specific choice of the most diverse phases and the addition of surfactant substances in one or more phases. In an especially preferred embodiment, different concentrations of a substance are arranged in the individual phases or sheets, so as to adjust a concentration gradient across the entire system, which enhances the selectivity and efficiency of the separation process.

It has been found to be especially advantageous to use, as the individual phases, liquid or gel sheets with a thickness in the submillimeter range or smaller, arranged in parallel with each other. Basically all known liquids or gels from classical electrophoresis can be used. When assembling the individual phases into a system, one can refer to experience in the field of separation by means of two-phase systems.

The invented device has a microfluid chamber and at least one pair of electrodes placed thereon, for applying an electric field. The microfluid chamber is filled with at least two nonmiscible fluids or gels in the form of at least one sheet each. The at least two sheets form a common phase boundary. When there are two or more sheets, there is one fewer phase boundary than the number of sheets. Depending on how the microfluid system is set up in the microfluid chamber, the applied electric field is perpendicular or parallel to the phase boundary or boundaries.

Especially in miniaturized form, the device can be termed a biochip. Biochips have analytical systems roughly the size of a credit card, already completed filled with the necessary fluids or gels. Ready filled biochips can be inserted directly into an evaluation unit, so that the analysis can be fully automated.

It is especially preferable for enhancing the selectivity to provide at least two pairs of electrodes, which generate two electric fields perpendicular to each other.

Depending on the number of phases and fluid sheets, as well as whether an electric field is to be applied only to one pair or to several, to one fluid sheet or to several, the overall number of electrode pairs will vary.

In a preferred embodiment, the device is configured in a planar geometry. This means that intake channels for each individual sheet and the microfluid chamber lie in the same plane. The intake channels correspond in their arrangement to the arrangement of the sheets in the microfluid system. The intake channels in which the individual fluid or gel phases are supplied in the form of sheets, are in flow connection with the microfluid chamber.

Chamber and intake channels are preferably provided with a cover.

In order to effectively apply electric fields by means of electrodes, the device should basically consist of nonconductive material, such as glass, plastic, or ceramic. Production from glass or glass ceramics is possible by means of UV lithography to produce the required structures. Glass or glass ceramics have the advantage of being chemically inert to many chemical substances and do not falsify the separation results.

In the cast of an especially low-cost embodiment, the invented device basically consists of plastic, which can be structured preferably by molding methods, such as injection molding, hot stamping or injection stamping.

The device is especially suitable for the separation of biomolecules and/or bioparticles. These may include, e.g., proteins, nucleic acids, DNA and cell fragments.

BRIEF DESCRIPTION OF THE DRAWINGS

The invention shall be explained more closely by means of the following drawings.

These show.

DETAILED DESCRIPTION OF THE INVENTION

Figure 1A:
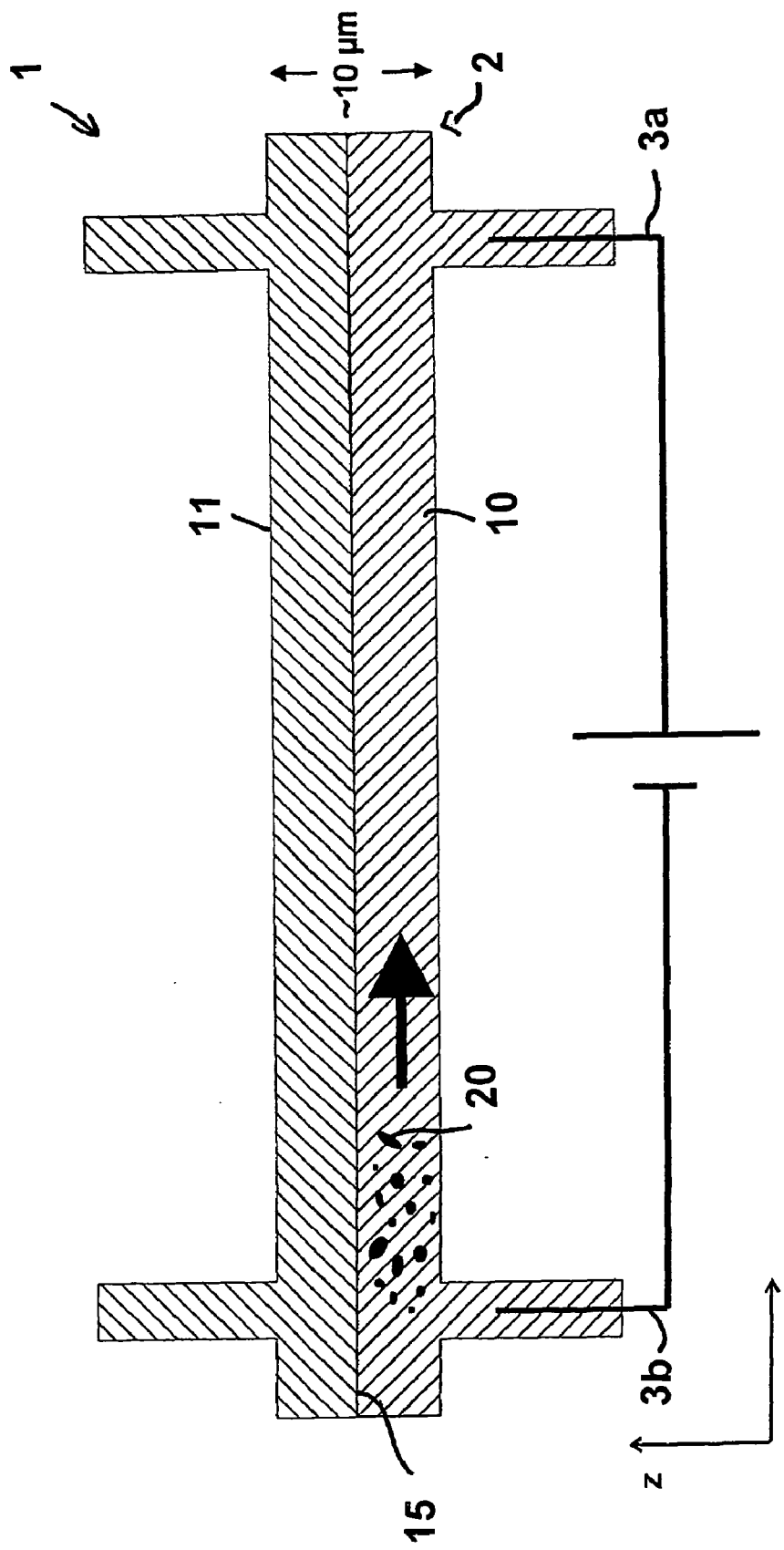
FIG. 1a, b: a first embodiment of the invented device.

The device 1 shown in FIG. 1a has a two-phase microfluid system in a microfluid chamber 2. The width of the microfluid chamber 2 is around 10 μm. One phase is an extraction fluid 11, and the other phase is a buffer solution 10. A d.c. voltage is applied via a pair of electrodes 3a, b to the buffer solution 10, parallel to the phase boundary 15.

The substances and particles 20 being separated are dissolved or suspended in the buffer solution 10. They can be proteins or nucleic acids or also subcellular fragments, such as cell nuclei, mitochondria, or vesicles.

The two nonmiscible fluids 10 and 11 in this example have no flow. But it can be advantageous to pump the fluids by means of a syringe, in order to counteract any electroosmotic flow which is present.

The biomolecules and bioparticles 20 are at first separated in the buffer solution 10, as during a normal capillary electrophoresis, in terms of their electrophoretic mobility, which is dependent on the charge and size of the respective molecules or particles. In the present example, however, the bioparticles and biomolecules 20 are also separated by their differing chemical affinity for the extraction phase 11 and their ability to pass through the fluid/fluid boundary layer. In this way, one achieves a multidimensional separation. The separation parameters can be influenced through the chemical composition of the extraction fluid 11, the addition of surfactant substances to the buffer solution, or also by applying an electric field perpendicular to the phase boundary.

Figure 1B:
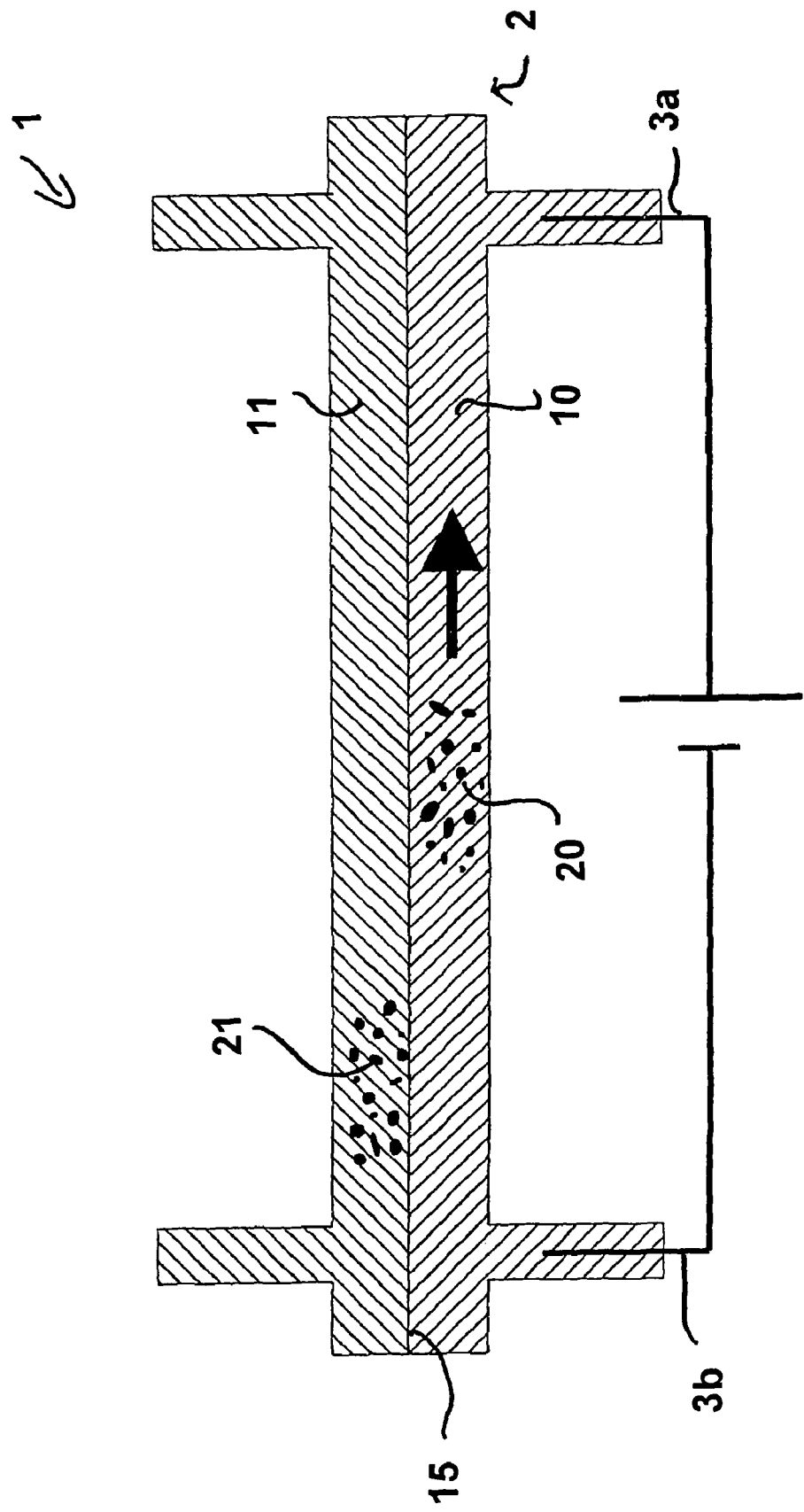

FIG. 1b shows the condition in which biomolecules 21 have separated themselves from the other biomolecules and bioparticles 20, having diffused increasingly into phase 11 by virtue of physicochemical affinity for this phase. Due to the voltage applied via the electrodes 3a, b, the other biomolecules and bioparticles 20 have already migrated toward the electrode 3a.

Figure 2:
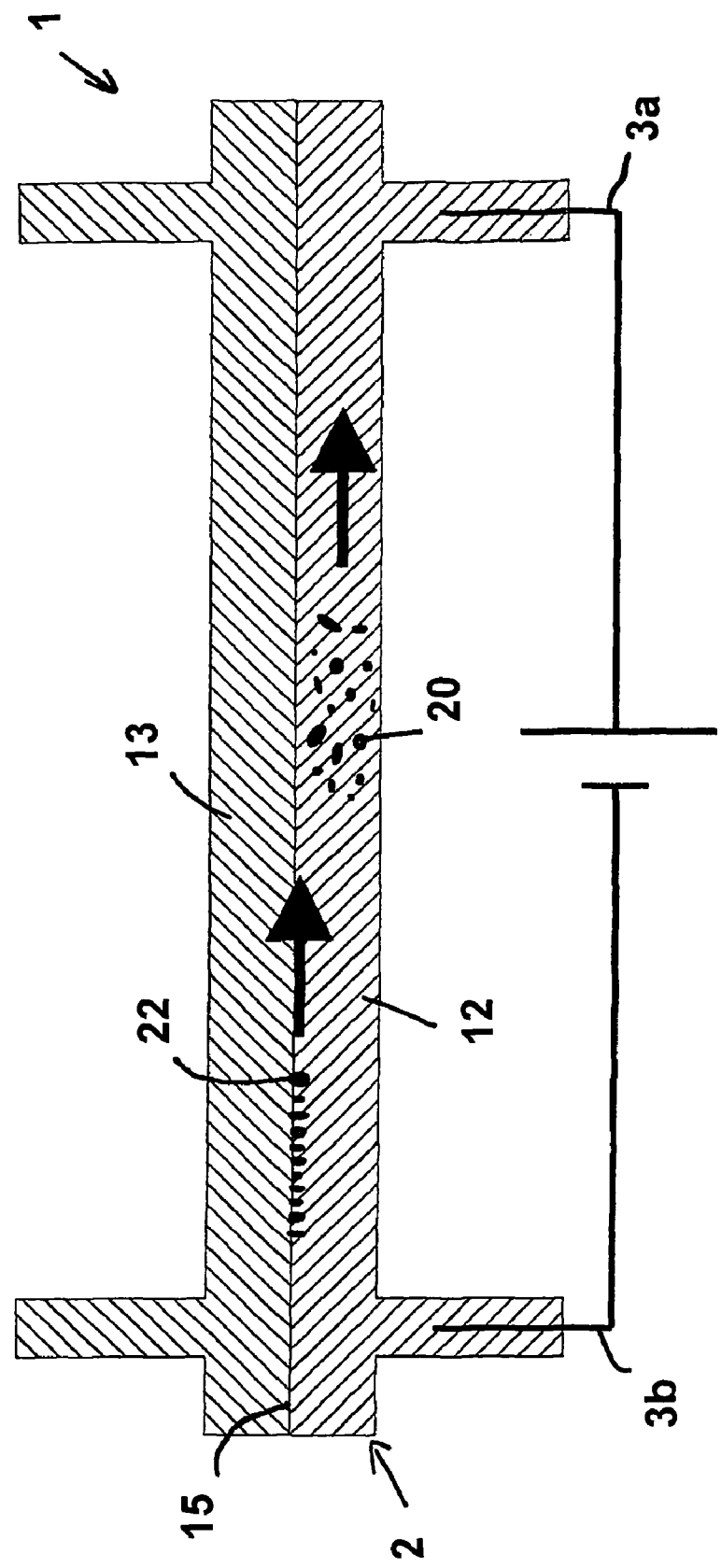
FIG. 2: a second embodiment of the invented device.

In FIG. 2, the phases 12, 13 are chosen such that many proteins 22 are accumulating at the phase boundary 15. If one furthermore chooses the phases 12 and 13 such that there is an aqueous and a nonaqueous phase, the mobility of the proteins 22 is determined by the distribution of the hydrophilicity or hydrophobicity over their surface. They line up at the phase boundary 15 in such a way that the hydrophobic parts dip into the nonaqueous phase 13 and the hydrophilic parts into the aqueous phase 12. With the help of the electric field applied via the electrodes 3a, b, they are electrophoretically separated. Totally hydrophobic proteins accumulate in the nonaqueous phase 13, totally hydrophilic proteins in the aqueous phase 12, where they are electrophoretically separated.

Figure 3:
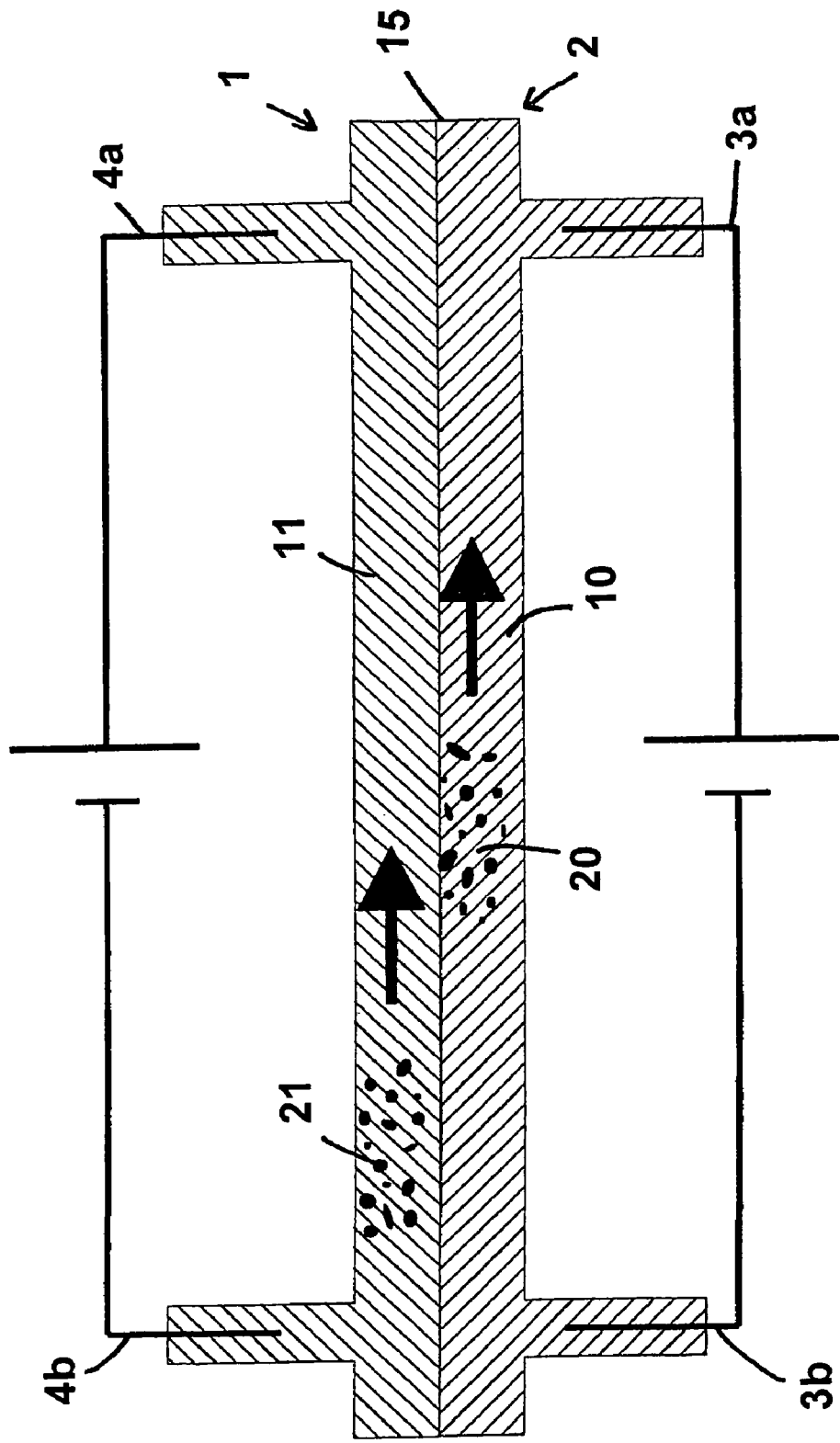
FIG. 3: a third embodiment of the invented device.

In another embodiment, shown in FIG. 3, once again a two-phase system of two nonmiscible aqueous solutions is used. Here they act as buffer solution 11 and as extraction solution. The substances and particles 21 diffusing by Brownian motion into the extraction phase 11 and accumulating there by virtue of chemical affinity are electrophoretically separated by means of a second electric field, which is applied by the electrodes 4a, b, again parallel to the phase boundary 15.

Figure 4:
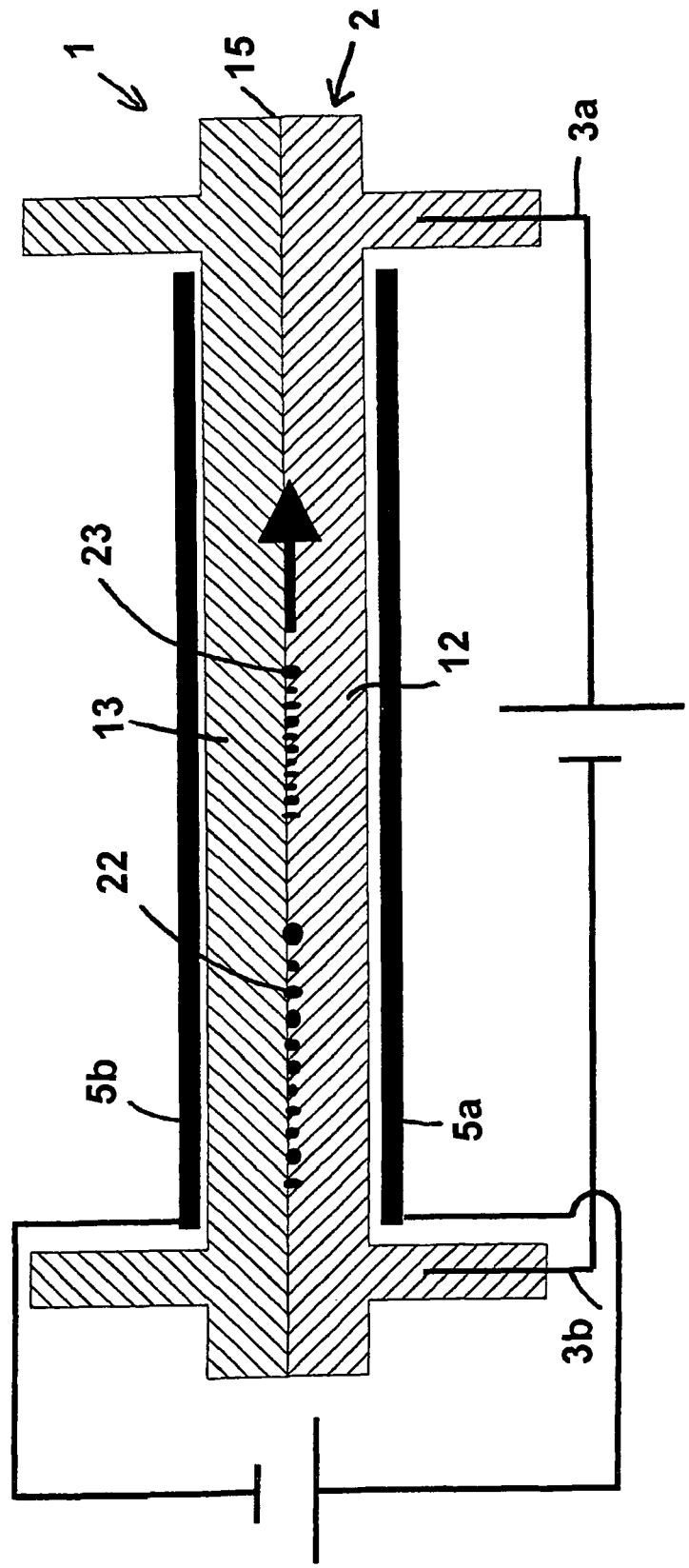
FIG. 4: a fourth embodiment of the invented device.

In the device 1 shown in FIG. 4, an additional electric field is applied via the electrodes 5a, b perpendicular to the phase boundary 15, and this over nearly the entire length of the microfluid chamber 2. The phase 12 is polar and the phase 13 is nonpolar. Furthermore, the two fluids 12, 13 have different viscosity. The electric field is adjusted perpendicular to the phase boundary 15 so that all biomolecules 22, 23 being separated accumulate at the phase boundary. The biomolecules 22, 23 become oriented, according to their hydrophobicity, so as to protrude more into the polar phase 12 or the nonpolar phase 13. Owing to the different viscosity and the electric field applied only to the polar phase parallel to the phase boundary 15, the biomolecules 22, 23 become separated by virtue of their surface properties and not so much by virtue of their size. Critical to the electrophoretic mobility in the present case are the distribution of the hydrophilicity and hydrophobicity on the molecular surface, their charge, their Dipole moment, and their $\zeta$-Potential.

Figure 5:
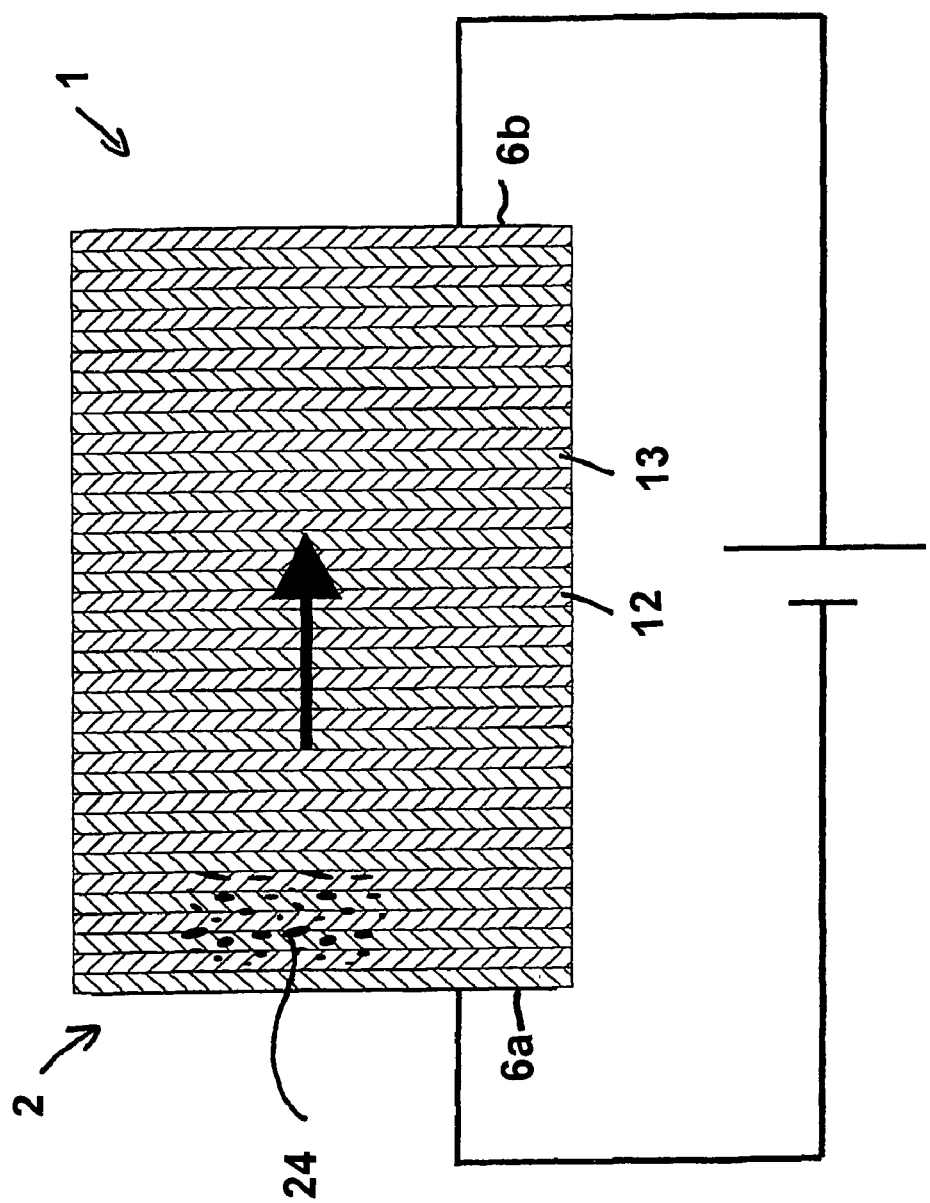
FIG. 5: a fifth embodiment of the invented device.

In the example per FIG. 5, the use of a multisheet system of two nonmiscible liquids 12 and 13 makes use of the fact that the electrophoretic mobility depends not only on the mobility in the individual phases 12, 13, but also to a large degree on the ability to penetrate the phase boundary. To make the multisheet system in the microfluid chamber 2, one can proceed on the same principle as for micromixers, with the difference that the laminar flow changes to a no-flow system. Any electroosmotic flow can be compensated by a pressure-generated counterflow. The parameters to be considered for setting up a multisheet system are the wetting ability of the microfluid chamber's walls, the surface tensions at the phase boundaries, and the density of the individual liquids. FIG. 5 includes electrodes 6a, 6b.

Figure 6:
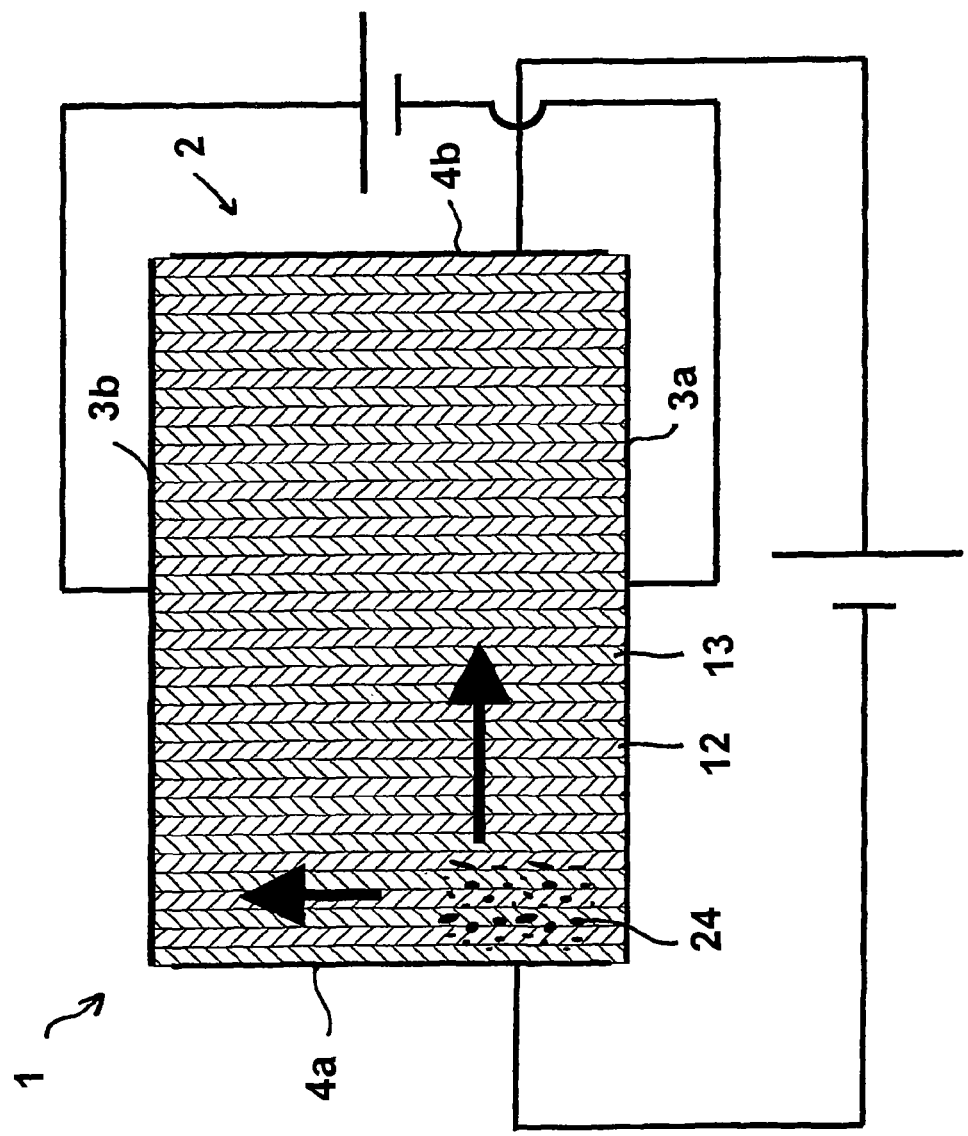
FIG. 6: a sixth embodiment of the invented device.

In the embodiment shown in FIG. 6, there is again a microfluid chamber 2 with a multisheet system. Electric fields are applied both parallel to the phase boundaries between the phases 12, 13 and also parallel to all phase boundaries. Parallel to the phase boundaries, this is done by means of the electrodes 3a, b; perpendicular to the phase boundaries, this is done through the electrodes 4a, b. The two fields are applied either at the same time or one after the other, depending on the mobility of the bioparticles and biomolecules 24 being separated in the individual phases and at the individual phase boundaries. If the field is at first applied perpendicular to the phase boundaries, the bioparticles and biomolecules 24 being separated are distributed over all sheets, and then the electric field parallel to the phase boundaries in each sheet is used for classical electrophoretic separation. In order to further enhance the selectivity of the separation perpendicular to the phase boundaries, a dissolved substance is present in one of the two phases, whose concentration varies from one sheet to another in the direction perpendicular to the sheets. In this way, the chemical affinity of the biomolecules and bioparticles 24 for the individual phases can be influenced.

Figure 7A:
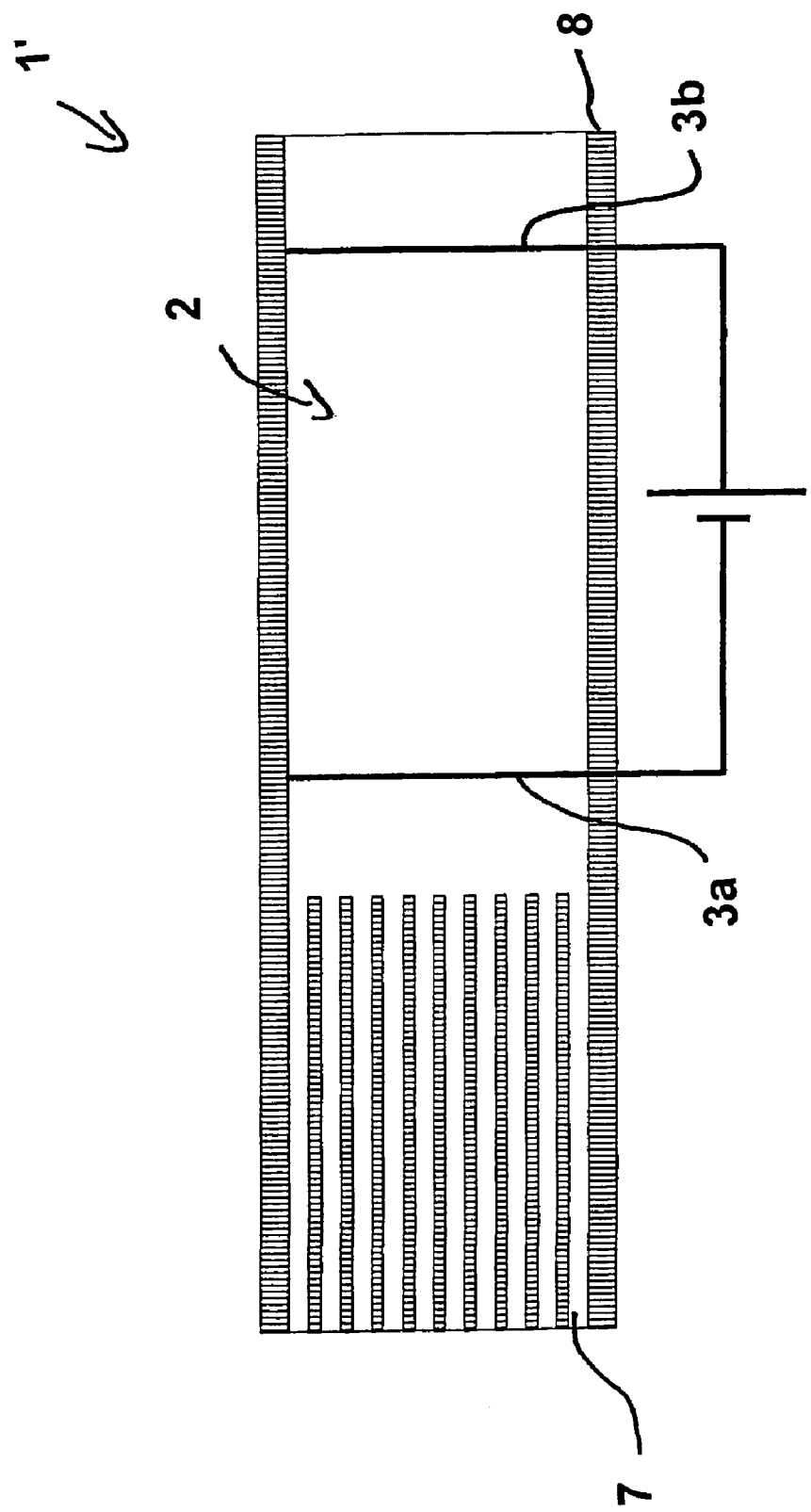
FIG. 7a, b: an embodiment as a biochip.
Figure 7B:
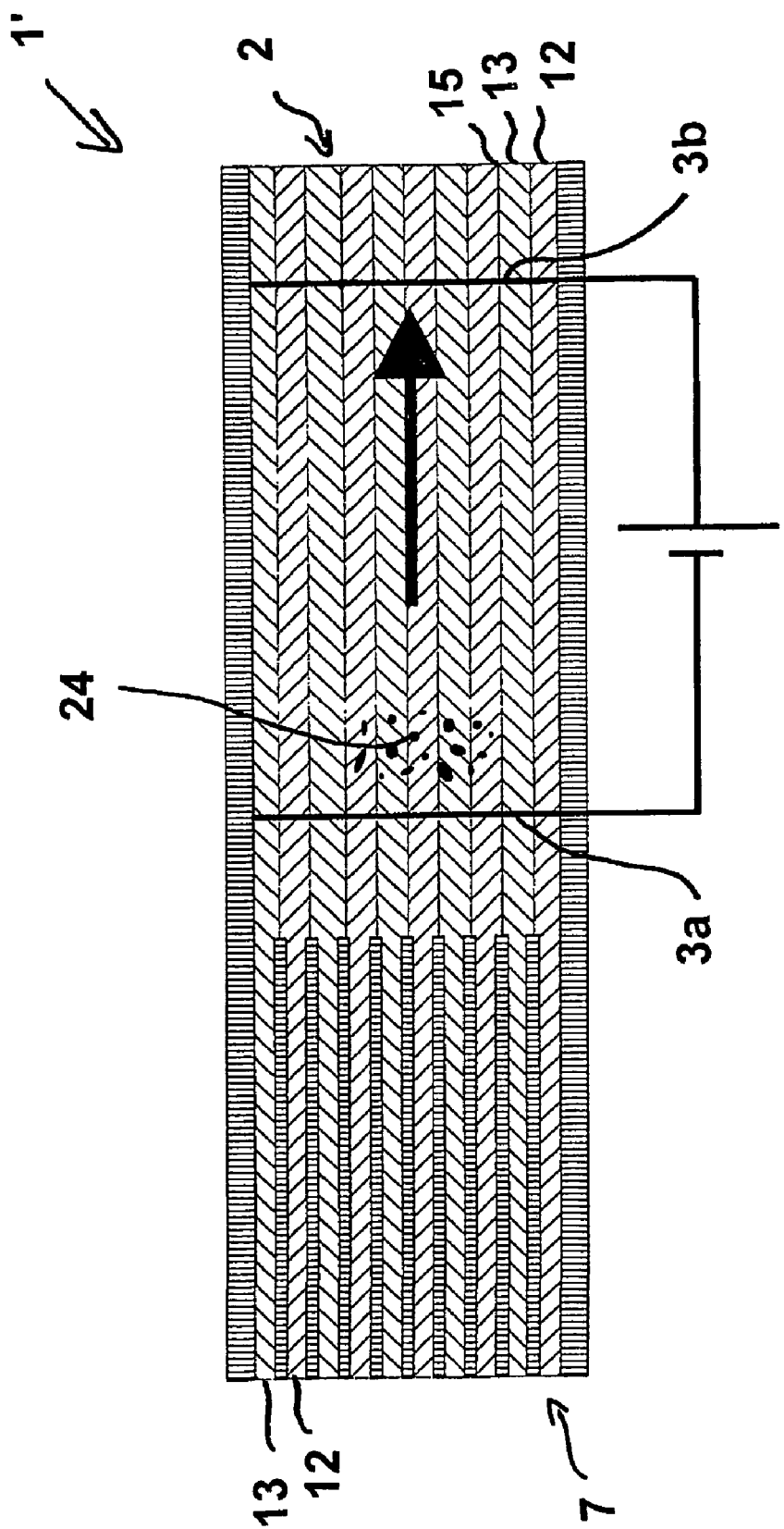

FIGS. 7a, b show an embodiment of the invented device as a biochip 1. For clarity, FIG. 7a shows an as yet unfilled biochip 1'. It consists essentially of a plate 8, which can also be called the substrate, in which recesses have been made, forming intake channels 7 on the one hand and the microfluid chamber 2 on the other. Not shown is a cover film, which closes over the intake channels 7 and chamber 1 on top. The intake channels 7 serve to supply the phases 12, 13 of nonmiscible fluids or gels (FIG. 7b). Depending on the application, there can also be more phases. Each intake channel 7 forms a sheet from the respective fluid or gel. Upon emerging from the intake channels 7, the sheets running parallel to each other abut against each other and form common phase boundaries 15. In the example shown in FIG. 7a, b, only one electrode pair 3a, b is provided, with its electric field parallel to the sheets. The number and kind of electrodes will be chosen as already discussed, according to the application.

It should be pointed out that all examples shown here can be realized with gels, instead of with liquids.

What is claimed is:

1. A method for separation of chemical substances and/or particles utilizing a microfluid chamber having intake channels and consisting of a plurality of parallel arranged adjoining liquid lamellae of two or more different phases having a thickness in the submillimeter range or smaller, comprising the steps of:

introducing liquid lamellae into said intake channels of said microfluid chamber, said microfluid chamber having a first electrode pair arranged thereon such that an electric field is generated parallel to the phase boundaries of the said liquid lamellae and a second electrode pair such that an electric field is generated perpendicular to the phase boundaries of said liquid lamellae; and flowing said liquid lamellae through said microfluid chamber while the electric field is applied by said first and second electrode pairs.

2. The method according to claim 1, wherein different concentrations of a substance having a given physicochemical affinity for the substances or particles or a combination thereof being separated are adjusted in the phases.

* * * * *